United States Patent [19]
Williams et al.

[11] Patent Number: 5,681,894
[45] Date of Patent: Oct. 28, 1997

[54] SOFT, FLEXIBLE TAMPON APPLICATOR AND METHOD FOR MAKING SAME

[75] Inventors: Karla E. Williams, Emerson, N.J.; Paul D. Zwick, Cuyahoga Falls, Ohio

[73] Assignee: Playtex Products, Inc., Westport, Conn.

[21] Appl. No.: 447,289

[22] Filed: May 22, 1995

[51] Int. Cl.$^6$ .......................... C08L 53/00; B29D 23/00; A61F 13/20

[52] U.S. Cl. .................... 525/89; 525/88; 601/11; 601/14; 601/15; 601/904; 428/35.7; 428/36.9

[58] Field of Search .................. 604/11, 12, 14, 604/15, 904; 525/88, 89; 428/36.9, 35.7

[56] References Cited

U.S. PATENT DOCUMENTS

| | | | |
|---|---|---|---|
| 3,765,416 | 10/1973 | Werner et al. | 604/18 |
| 3,807,399 | 4/1974 | Morman et al. | 604/14 |
| 3,895,634 | 7/1975 | Berger et al. | 604/14 |
| 4,678,834 | 7/1987 | Boivin et al. | 525/74 |
| 5,135,475 | 8/1992 | Nakanishi et al. | 604/14 |

Primary Examiner—Mark L. Warzel
Attorney, Agent, or Firm—Ohlandt, Greeley, Ruggiero & Perle

[57] ABSTRACT

There is provided a tampon applicator, particularly an applicator barrel, comprising a unique compound to provide a soft, flexible applicator barrel that is more comfortable and has improved ease of insertion. The polymeric compound primarily comprises a thermoplastic resin and a block copolymer that exhibit unique load, energy and modulus of elasticity properties. The polymeric compound should also include a plasticizer and a compatibilizer/flow modifier, and may include a slip/mold release agent, and antioxidants, and even a pigment. There is also provided a method for making the polymeric compound that will be formed into an applicator or applicator barrel in which all of the above ingredients, except for the thermoplastic resin, are combined and formed into soft pellets. The soft resin pellets are then dry blended with pellets of the thermoplastic resin. The mixture of the thermoplastic resin pellets and the soft resin pellets are then melted and injection molded into the desired shape of the applicator or applicator barrel.

21 Claims, No Drawings

SOFT, FLEXIBLE TAMPON APPLICATOR AND METHOD FOR MAKING SAME

BACKGROUND OF THE INVENTION

1. Field of the Invention

The present invention relates generally to tampon applicators. More particularly, the present invention relates to a soft, flexible tampon applicator barrel to provide comfort and ease of insertion into a vagina.

2. Description of the Prior Art

Polyethylene is a thermoplastic that is the standard resin used to produce plastic tampon applicators. Users desire more comfortable applicators. Softness is a feature of comfort. A softer applicator, especially an applicator barrel, that is more comfortable is a desirable feature of a tampon applicator in order to provide improved ease of insertion.

It is generally known that thermoplastic elastomer articles may be combined with polyethylene to improve the strength and toughness of such articles. For example, U.S. Pat. No. 4,593,063 to M. A. Jones, et al., which issued Jun. 3, 1986, provides a reinforced rigid polymer blend which yields a high gloss finish when injection molded. The thermoplastic elastomer includes 25 to 35 percent of a butadiene thermoplastic elastomer having a molecular weight of about 70,000 to about 100,000, a styrene content of from about 25 to about 44 percent by weight and a melt flow rate of from about 8 to about 15 grams per 10 minutes. The butadiene thermoplastic elastomer is blended with from about 54 to about 75 percent of a rigid polymer, such as polyethylene.

Polymers have also been combined with polyethylene to improve their reaction to each other when heated or otherwise processed. For example, U.S. Pat. No. 4,678,834 to D. W. Boivin, et al., which issued Jul. 7, 1987, provides a polyolefin blend comprising a major portion of polyethylene and a minor portion of a second polymer, such as a styrene-butadiene-styrene copolymer. The second polymer contains a reactive agent that is capable of reacting with polyolefins in a molten state. The reactive agent modifies or stabilizes the polymer during processing or during use.

Polymers may also be added to polyethylene to permit a breakdown of its structural composition. Polyethylene, which is normally stable, has also been combined with less stable materials to produce biodegradable products. Such biodegradable products include ingredients that cause oxidative actions in order to break down the polyethylene. For example, U.S. Pat. No. 5,212,219 to G. J. L. Griffin, which issued May 18, 1993, provides a degradable article prepared from a blend of polyethylene and a less stable polymer or copolymer, such as a styrene-butadiene block copolymer. The composition further comprises of an antioxidant active over a limited period and a pro-oxidant that causes a sharp loss of physical strength on depletion of the anti-oxidant. In addition, the presence of filler particles of a biologically sensitive material accelerates the biological breakdown of the polymer/copolymer blend.

Improvements to the pelletizability and drapability of a polymer composition, without causing the composition to biodegrade, are also known. For example, U.S. Pat. No. 4,833,195 to A. M. Adur, et al., which issued May 23, 1989, provides a thermoplastic polymer composition that can be conveniently converted into a drapable film or fabric. The composition has a low Shore A hardness, i.e., below about 95, and a high melt flow rate of about 30 grams/10 minutes to 1100 grams/10 minutes at 230 degrees Celsius and 2.16 kilograms. Drapability is an important property of products that drape against a user's skin, such as baby diapers or sanitary napkins.

However, none of the above patents describe or suggest a tampon applicator that is composed of such materials. Moreover, none of the above patents suggest a combination of polyethylene and a particular rubber composition to improve its softness and flexibility. Thus, the above patents do not suggest a soft, flexible tampon applicator having a unique blend of polyethylene and a rubber type composition that includes a block copolymer, namely a styrene-butadiene-styrene block copolymer, which applicator provides for comfortable and easy insertion into a vagina.

Further, thermoplastic resins are much less expensive than elastomeric materials. To minimize the costs of tampon applicators, one desires to have as great as possible an amount of thermoplastic resin in the composition. Accordingly, to achieve the benefits of a flexible and easy to insert tampon applicator barrel and yet minimize costs, it is desired to use as little as possible of the elastomer components and as much as possible of the thermoplastic resin component in the tampon applicator barrel.

SUMMARY OF THE INVENTION

Against the foregoing background, it is a primary object of the present invention to provide a thermoplastic-type tampon applicator, particularly its applicator barrel, that is soft and flexible to provide more comfort and improved ease of insertion.

It is another object of the present invention to provide such a tampon applicator with the desired properties of an elastomer to achieve the characteristics of a soft, flexible tampon applicator.

It is a further object of the present invention to provide such a tampon applicator with the desired properties of at least one styrene-butadiene-styrene block copolymer to achieve such characteristics.

To accomplish the foregoing objects and advantages, the present invention, in brief summary, is a tampon applicator barrel that is soft and flexible for more comfort and improved ease of insertion into a vagina. The tampon applicator barrel comprises a thermoplastic resin and at least one block copolymer in amounts sufficient to adjust the elasticity of the tampon applicator barrel so that the modulus of elasticity of the tampon applicator barrel is less than 42 lbs. per square inch. In a more preferred embodiment, the tampon applicator barrel has a modulus of elasticity less than about 35 lbs. per square inch.

More specifically, the present invention is a soft, flexible tampon applicator that provides more comfort and improved ease of insertion into a vagina. The applicator comprises a low density polyethylene and at least one styrene-butadiene-styrene block copolymer.

In a most preferred embodiment, there are three styrene-butadiene-styrene block copolymers each having a percentage by weight of styrene that is different than that of the other two block copolymers. In particular, the first styrene-butadiene-styrene block copolymer has about 29 percent by weight of styrene in the block copolymer, the second styrene-butadiene-styrene block copolymer has about 31 percent by weight of styrene, and the third styrene-butadiene-styrene block copolymer has about 43 percent by weight of styrene.

The polymeric resin should further comprise one or more of the following: a plasticizer and a compatibilizer/flow modifier, may further comprise other ingredients, such as a pigment, a slip/mold release agent, and an antioxidant and, perhaps, an antistat ingredient.

The present invention is also a method for making a tampon applicator, especially an applicator barrel, that has a soft and flexible structure for more comfort and improved ease of insertion into a vagina. An elastomer composition is melted and combined to form a melted resin. The melted resin is then extruded into a plurality of soft resin pellets. The plurality of soft resin pellets are then dry blended with a plurality of pellets of a low density polyethylene to form a pellet mixture. Finally, the pellet mixture is melted together to form a polymeric compound in which the polymeric compound may be molded to a desired shape for the tampon applicator barrel.

DETAILED DESCRIPTION OF THE PREFERRED EMBODIMENT

The present invention provides a tampon applicator, particularly an applicator barrel, composed of a new polymeric compound. As stated above, to minimize costs, it is preferable that the tampon applicator have an applicator barrel that uses the polymeric compound of the present invention while the plunger be made of a standard material since a softer applicator barrel is more comfortable and is a desirable feature of a tampon applicator in order to provide improved ease of insertion. Accordingly, the present application is directed to a tampon applicator barrel, however it can be used for the entire tampon applicator.

The polymeric resin comprises polyolefin and a rubber type composition that adjusts the softness and flexibility of the polymeric compound and, thus, the tampon applicator. For the preferred embodiment, the polyolefin is a low density polyethylene and the rubber type composition includes a thermoplastic elastomer. The thermoplastic elastomer is one or more block copolymers. In the most preferred embodiment, the thermoplastic elastomer is a plurality of styrene-butadiene-styrene block copolymers.

The primary supporting structure of the soft applicator barrel is provided by the polyolefin. The preferred type of polyolefin is polyethylene, as stated above, and more preferably, low density polyethylene. The polyethylene can be a linear low density polyethylene. For the preferred embodiment, the polyolefin is about 25 to about 75 percent by weight of the total weight of the polymeric compound.

The rubber type composition includes a plurality of thermoplastic elastomers. The thermoplastic elastomers are combined with the polyolefin in amounts sufficient to adjust the elasticity of the polymeric compound. As indicated by testing for the preferred embodiment, described below, the modulus of elasticity of the polymeric compound is less than about 42 lbs. per square inch, and most preferably less than about 35 lbs. per square inch.

Styrene-butadiene-styrene block copolymers are the preferred thermoplastic elastomers. A combination of three different types of styrene-butadiene-styrene block copolymers having different contents of styrene is the most preferred. For the first preferred embodiment, a first styrene-butadiene-styrene block copolymer has 29 percent by weight of styrene in the block copolymer, a molecular weight of 80,000 and a melt flow rate of 8 gram per 10 minutes, a second styrene-butadiene-styrene block copolymer has 31 percent by weight of styrene, a molecular weight of 100,000 and a melt flow rate of less than 1 gram per 10 minutes, and a third styrene-butadiene-styrene block copolymer has 43 percent by weight of styrene, a molecular weight of 58,000 and a melt flow rate of 23 gram per 10 minutes. The melt flow rate for all three styrene-butadiene-styrene block copolymers is measured at 200 degrees Celsius with a 5.0 kg load. Such styrene-butadiene-styrene block copolymers are commercially available as Vector Resin 8550, Vector Resin 2518, and Vector Resin 6241 for the first, second and third styrene-butadiene-styrene block copolymers, respectively. These copolymers are manufactured by Dexco Polymers (a Dow/Exxon Partnership) of Houston, Texas.

Each of the first, second and third styrene-butadiene-styrene block copolymers is about 5.5 to about 16.6 percent by weight of the total weight of the polymeric compound. Accordingly, the weight of the block copolymers is about 16.5 to about 49.80 by weight of the total weight of the polymeric compound.

The combination of these three block copolymers has been found to provide the optimum viscosity desired so that the thermoplastic resin phase, namely polyethylene, and the rubber phase are compatible.

The rubber type composition that is added to the polyolefin may also include other materials. It is preferred that a plasticizer, such as mineral oil, to reduce its viscosity and hardness also be included. The plasticizer is about 5 to about 15 percent by weight of the total weight of the polymeric compound.

It is also preferred that the polymeric compound include a compatibilizer/flow modifier, which assists in the blending or compatibilization of the thermoplastic resin and the rubber materials, and to improve the properties. The compatibilizer/flow modifier is a copolymer. In the preferred embodiments, the copolymer is an ethylene copolymer. It is believed, however, that other copolymers such as, for example, an alpha olefin copolymer, may be used. In the most preferred embodiment, the ethylene copolymer is ethylene methyl acrylate. Alternative alpha olefin copolymers that can be used are ethylene vinyl acetate, ethylene ethyl acrylate, ethylene butyl acrylate. Ethylene methyl acrylate is the most preferred since it, unlike ethylene vinyl acetate, will not decompose under high molding temperatures, and is less expensive than either ethylene ethyl acrylate or ethylene butyl acrylate.

The compatibilizer/flow modifier is present in an amount about 2.9 to about 8.6 percent by weight of the total weight of the polymeric compound.

The rubber type composition may further include additives, such as a pigment or color additive, a slip/mold release agent, an antioxidant and an antistat, that are necessary to ease the manufacture or otherwise improve the quality of the tampon applicator or barrel.

The pigment, that is chosen to provide the desired aesthetic effect, is preferably titanium dioxide. It is about 0.5 to about 1.5 percent weight of the total weight of the polymeric resin.

The slip/mold release agent is, preferably, a fatty acid amide, such as erucamide which is sold under the name Kemamide E by Humko of Memphis, Tenn. Alternatively, the slip/mold release agent can be a calcium stearate, stearyl erucamide, ethylene bis stearamide and ethylene bis oleamide. The slip/mold release agent is about 0.4 to about 1.1 percent by weight of the total weight of the polymeric compound.

The antioxidant provides stability to the polymeric compound. It is preferred that the antioxidant be a combination of two antioxidants. One antioxidant is tetrakis [methylene (3,5-di-tert-butyl-4-hydroxyhydrocinnamate)] methane. The other antioxidant is tris (2,4-di-tert-butyl phenyl) phosphite. Such antioxidant/stabilizer is manufactured under the product name Irganox 1010 by Ciba-Geigy Corporation. Each antioxidant is about 0.05 to about 0.15 percent by weight of the total weight of the polymeric compound.

The most preferred embodiment of the present soft applicator has the following ingredients and their approximate percent composition by weight:

| | |
|---|---|
| 58% | low density polyethylene; |
| 9% | first styrene-butadiene-styrene block copolymer having about 29 percent of styrene; |
| 9% | second styrene-butadiene-styrene block copolymer having about 31 percent of styrene; |
| 9% | third styrene-butadiene-styrene-block copolymer having about 43 percent of styrene; |
| 8% | mineral oil as the plasticizer; |
| 5% | ethylene methyl acrylate as the compatabilizer/flow modifier; |
| about 1% | titanium dioxide as the pigment; |
| about 1% | erucamide as the slip/mold release agent; |
| less than 1% | tetrakis [methylene (3,5-di-tert-butyl-4-hydroxyhydrocinnamate)] methane as an antioxidant; and |
| less than 1% | tris (2,4-di-tert-butyl phenyl)phosphite as an antioxidant. |

Higher styrene contents would tend to make the elastomer material less soft and less flexible. In a preferred embodiment of the polymeric compound, the amount of the third styrene-butadiene-styrene block copolymer is about one-half of one percent less than the amount of the first or second styrene-butadiene-styrene block copolymers.

It is to be understood that an antistatic agent or antistat may be added to the polymeric compound but is not a part of the preferred embodiment. The antistat imparts a slight to moderate degree of electrical conductivity to plastic compounds, thus preventing the accumulation of electrostatic charges on soft applicator. The antistat may be incorporated in the ingredients before molding, or applied to the outer surface of the tampon applicator or barrel after molding.

The preferred method for making the preferred polymeric compound that is formed into an applicator or applicator barrel is as follows. The three styrene-butadiene-styrene block copolymers, mineral oil, ethylene methyl acrylate, erucamide and the antioxidants (and pigment, if used) are weighed and then combined in a twin screw extruder that melts and blends the ingredients and forms a melted resin. The melted resin is then extruded and cut into soft resin pellets. These soft resin pellets are then dry blended with pellets of the remaining ingredient, i.e., the low density polyethylene, to form a pellet mixture. The pellet mixture of low density polyethylene pellets and soft resin pellets are then melted and injection molded to form the desired shape for the soft tampon applicator or applicator barrel.

An alternative method for making the preferred polymeric compound that is formed into an applicator or applicator barrel includes weighing all ingredients including the low density polyethylene and then combining them in a twin screw extruder to form the melted compound. The melted compound is then extruded and cut into pellets and injection molded to form the desired shape for the tampon applicator or applicator barrel.

In order to exemplify the effectiveness of the composition comprising low density polyethylene and styrene-butadiene-styrene block copolymers verses conventional low density polyethylene based compositions, the following comparison tests were conducted of tampon applicator barrels.

EXAMPLE 1

The preferred polymeric resin when used in an applicator barrel technically, as measured by Shore hardness and flex modulus, is softer than the thermoplastic currently used in known thermoplastic tampon applicator barrels. To demonstrate a difference in "softness" between the subject applicator barrel and the known tampon applicator barrels, it was necessary to test the hardness, Shore A or Shore D. As known in the art, Shore hardness, also known as indentation hardness, of a material is determined by the indentation made by an indenting tool under a fixed load or load necessary to produce penetration of the indenter to a predetermined length. The scale readings range from 0 for 0.100" penetration to 100 for zero penetration. A Shore A hardness test employs a sharp indentor point with a load of 822 grams, and a Shore D hardness test employs a blunt indentor point with a load of 10 lbs.

The known thermoplastic tampon applicator barrels included Tampax, Kotex's Security, Kotex's curved, and Playtex. All four are polyethylene applicator barrels, however they appear to be of different grades of polyethylene and/or have different additives.

The Shore A hardness of the soft applicator barrel is about 92 using test method ASTM D2240. All known thermoplastic-type tampon applicator barrels have a Shore A hardness beyond the scale, i.e. greater than 100.

The present applicator has also been found to have a Shore D hardness of about 27, whereas the Shore D hardness of three known thermoplastic-type applicator barrels (Kotex curved was not measured) is approximately 34 to 42. These test results illustrate the soft character of the polymeric compound of the preferred embodiment.

EXAMPLE 2

Another element of "softness" is flexibility. In order to test for flexibility, Instron compression testing had been performed to compare differences in flexibility of the tampon applicator barrel of the preferred embodiment against the four known thermoplastic applicator barrels.

Instron compression test was designed to treat the whole barrel as a tubular specimen. A ⅝ inch wide platen is used to radially compress the applicator barrel against a 6 inch anvil. The specimen is placed on the anvil so that the platen engages the barrel at an axial location between 1⅜ inch and 2 3/16 inch as measured from the finger grip end of the applicator barrel. The specimen is compressed by a total of 0.25 inch at a rate of 0.5 inch/minute.

As shown in Table B below, the Instron compression test produced the following results for the preferred embodiment of the soft applicator.

TABLE B

| Instron Compression Testing | | |
|---|---|---|
| LOAD lbs. (std. dev.) | YOUNG'S MODULUS PSI (std. dev.) | ENERGY lbs.-inch (std. dev.) |
| Tampon applicator barrels having a diameter about 0.67 inches ± .07 inches and a wall thickness about .027 inches ± .003 inches | | |
| Known Branded Thermoplastic applicators | | |
| 2.27 to 3.75 (0.18 to 0.22) | 49.20 to 73.40 (4.80 to 9.80) | 0.30 to 0.50 (0.03 to 0.04) |
| Present Applicator | | |
| 1.18 (0.08) | 22.03 (2.27) | 0.15 (0.01) |
| Tampon applicator barrels having a diameter about 0.56 inches ± .06 inches and a wall thickness about .027 inches ± .003 inches | | |

TABLE B-continued

Instron Compression Testing

|  | LOAD lbs. (std. dev.) | YOUNG'S MODULUS PSI (std. dev.) | ENERGY lbs.-inch (std. dev.) |
|---|---|---|---|
| Known Branded Thermoplastic applicators | 2.61 to 4.90 (0.19 to 0.21) | 74.30 to 120.70 (7.80 to 15.39) | 0.33 to 0.61 (0.04 to 0.05) |
| Present Applicator | 1.54 (0.11) | 31.26 (3.54) | 0.19 (0.02) |

The standard deviation of the four known branded thermoplastic applicator barrels is different for each applicator barrel. It should be understood that the grade of material, diameter and wall thickness are the three factors that affect flexibility, and that flexibility is determined by the load, Young's modulus or modulus of elasticity, and energy.

Young's modulus is a measurement for flexibility, also known in the art as modulus of elasticity, that is the ratio of a nominal stress to corresponding strain below the proportional limit of a material. Young's modulus is expressed in force per unit area, usually lbs. per square inch as shown in Table B.

As shown in Table B, the present applicator is significantly more flexible than known thermoplastic applicators. For the larger diameter applicator barrels (0.67 inches +/−0.07 inches), the load results indicate that the applicator barrel made with the preferred polymeric compound requires about 1.18 lbs. to radially compress the applicator barrel by 0.25 inches, whereas the four known thermoplastic applicator barrels require about 2.27 lbs. per square inch to about 3.75 lbs. In addition, Young's modulus or the modulus of elasticity for the present applicator barrel is about 22 lbs. per square inch, whereas the known thermoplastic applicators is about 49 lbs. per square inch to about 73 lbs. per square inch. Also, the energy to compress by 0.25 inches the present applicator barrel is about 0.15 lbs.-inch. whereas the known applicator barrels are about 0.30 to 0.50 lbs.-inch. Preferably, the larger diameter barrel will have a supportable load of less than 1.24 lbs., as measured by Instron Compression Testing, a modulus of elasticity of less than about 24 lbs. per square inch, and the energy to compress the basel by 0.25 inches will be less than 0.16 lbs.-inch.

For the smaller diameter applicator barrels (0.56 inches +/−0.06), the load results indicate that the applicator barrel made with the preferred polymeric compound requires about 1.54 lbs. to radially compress the applicator barrel, whereas the known thermoplastic applicator barrels require about 2.61 lbs. per square inch to about 4.90 lbs. In addition, the modulus of elasticity for the present applicator barrel is about 31 lbs. per square inch, whereas the known thermoplastic applicator barrels are about 74 lbs. per square inch to about 121 lbs. per square inch. Also, the energy to compress by 0.25 inches. the present applicator barrel is about 0.19 lbs.-inch. whereas such energy to compress the known applicator barrels is about 0.33 to 0.61 lbs.-inch. Preferably, a barrel having this diameter and wall thickness will have a supportable lead of less than about 1.65 lbs., as measured by Instron Compression Testing, a modulus of elasticity in the range of less than 27 to about 35 psi, and will require less than 0.21 lbs.-inch to radially compress the tampon applicator barrel by 0.25 inches.

Thus, the present or soft applicator made with the preferred polymeric compound of the present invention has a load, modulus of elasticity and energy approximately one-half that of all known thermoplastic applicator barrels. In addition, the applicator barrel of the present invention has been found by consumers as a unique, softer applicator barrel due to the tactile feel of the applicator barrel.

The present invention having been thus described with particular reference to the preferred forms thereof, it will be obvious that various changes and modifications may be made therein without departing from the spirit and scope of the invention as defined in the appended claims.

Wherefore, we claim:

1. A tampon applicator barrel comprising:
   a thermoplastic resin; and
   a block copolymer in amounts sufficient to adjust the elasticity of the tampon applicator so that the modulus of elasticity of the tampon applicator is less than about 42 psi, wherein said block copolymer comprises a plurality of three block copolymers.

2. The tampon applicator barrel of claim 1, wherein the modulus of elasticity is less than 35 psi.

3. The tampon applicator barrel of claim 1, wherein the tampon applicator barrel has a diameter of about 0.67 inches and a wall thickness of about 0.27 inches, and the modulus of elasticity is less than about 24 psi.

4. The tampon applicator barrel of claim 1, wherein the tampon applicator barrel has a diameter of about 0.56 inches and a wall thickness of about 0.27 inches, and the modulus of elasticity is less than about 27 to about 35 psi.

5. The tampon applicator barrel of claim 1, wherein said plurality of three block copolymers is present in an amount sufficient to adjust the energy needed to radially compress the tampon applicator barrel by 0.25 inches to less than about 0.21 lbs.-inch.

6. The tampon applicator barrel of claim 1, wherein said plurality of three block copolymers is present in an amount sufficient to adjust the supportable load of the tampon applicator barrel to less than about 1.65 lbs.

7. The tampon applicator barrel of claim 3, wherein said plurality of three block copolymers is present in an amount sufficient to adjust the energy needed to radially compress the tampon applicator barrel by 0.25 inches to less than about 0.16 lbs.-inch.

8. The tampon applicator barrel of claim 3, wherein said plurality of three block copolymers is present in an amount sufficient to adjust the supportable load of the tampon applicator barrel to less than about 1.24 lbs.

9. The tampon applicator barrel of claim 1, wherein the thermoplastic resin is a polyolefin.

10. The tampon applicator barrel of claim 9, wherein the polyolefin is a low density polyethylene.

11. The tampon applicator barrel of claim 10, wherein the low density polyethylene is linear low density polyethylene.

12. The tampon applicator barrel of claim 1, further comprising a compatibilizer/flow modifier.

13. The tampon applicator barrel of claim 12, wherein said compatibilizer/flow modifier is an ethylene copolymer.

14. The tampon applicator barrel of claim 13, wherein said ethylene copolymer is ethylene methyl acrylate.

15. The tampon applicator barrel of claim 1, further comprising a plasticizer.

16. The tampon applicator barrel of claim 15, wherein said plasticizer is mineral oil.

17. The tampon applicator barrel of claim 1, further comprising a slip/mold release agent.

18. The tampon applicator barrel of claim 17, wherein said slip/mold release agent is erucamide.

19. The tampon applicator barrel of claim 1, further comprising an antioxidant.

20. The tampon applicator barrel of claim 19, wherein said antioxidant is at least two antioxidants.

21. The tampon applicator barrel of claim 20, wherein said at least two antioxidants are tetrakis [methylene (3,5- di-tert-butyl-4-hydroxyhydrocinnamate)] methane and tris (2,4-di-tert-butyl phenol) phosphite.

* * * * *